United States Patent [19]

Nickell et al.

[11] Patent Number: 4,559,080
[45] Date of Patent: Dec. 17, 1985

[54] 6-AMINO-2-ETHYLTHIO-4-PYRIMIDINOL AS A CITRUS RIPENER

[75] Inventors: Louis G. Nickell, Chicago; Leonard J. Stach, Riverside, both of Ill.

[73] Assignee: Velsicol Chemical Corporation, Chicago, Ill.

[21] Appl. No.: 703,075

[22] Filed: Feb. 19, 1985

[51] Int. Cl.⁴ .............................................. A01N 43/54
[52] U.S. Cl. .......................................... 71/92; 426/616
[58] Field of Search ............... 426/533, 537, 616, 419, 426/442, 534, 333, 308, 302, 135, 331; 544/312; 427/4; 71/92

[56] References Cited

U.S. PATENT DOCUMENTS 3,118,754  1/1964  Nickell ..................................... 71/92
4,281,021  7/1981  Iezuka et al. ......................... 426/302

FOREIGN PATENT DOCUMENTS 4627689  3/1968  Japan ....................................... 71/91

OTHER PUBLICATIONS

Tsuji et al, 1962, Chem. Bull (Tokyo) vol. 10, pp. 9-13.

*Primary Examiner*—Raymond Jones
*Assistant Examiner*—Carolyn Paden
*Attorney, Agent, or Firm*—Robert J. Schwarz

[57] ABSTRACT

The subject matter of this invention is the use of 6-amino-2-ethylthio-4-pyrimidinol and its water-soluble salts to lessen the acidity and increase the Brix/acid ratio of citrus.

11 Claims, No Drawings

6-AMINO-2-ETHYLTHIO-4-PYRIMIDINOL AS A CITRUS RIPENER

This invention relates to the use of 6-amino-2-ethylthio-4-pyrimidinol and its water-soluble salts to lower the acid content of citrus and increase its Brix/acid ratio. The term "citrus" includes, but is not limited to, tangerines, oranges, limes, lemons, grapefruit, and related plants. The term "salts" includes potassium, sodium, ammonium, dimethylamine, and other water-soluble salts.

In order to obtain a premium market price for citrus it is necessary that it have the highest possible internal quality including among other factors good taste and low acidity. Improvement in the various internal quality factors has been practiced for many years by the application of plant regulators. Improvement of citrus flavor has been practiced for many years in Florida through the use of lead arsenate.

Lead arsenate causes a reduction in the total acidity of grapefruit and consequently an increase in the Brix/acid ratio. It is also effective on oranges, but its use on oranges is illegal in Florida. Research has shown that most arsenical compounds appear to have commercial possibility in oranges.

Furthermore the use of lead arsenate and other arsenates has been considered to be a possible health hazard as inorganic arsenates are considered to be possible carcinogens. Thus there is the likelihood that the use of inorganic arsenates will not be permitted to continue. Consequently, there is a strong need for the development of new materials for use as citrus ripeners.

It has now been found that 6-amino-2-ethylthio-4-hydroxypyrimidine lowers the acidity of citrus and increases the Brix/acid ratio. This compound may be applied as the alcohol or as a water-soluble salt. It is reported in the literature by Tsuji et al. in *Chem. Pharm. Bull.* (Tokyo), Vol. 10, p. 9–13 (1962). The material used in the present tests was prepared as follows:

EXAMPLE 1

6-Amino-4-hydroxy-2-mercaptopyrimidine (143 grams; 1.0 mole), sodium ethoxide (68 grams; 1.0 mole), bromoethane (140 grams; 1.3 mole) and absolute ethanol (1000 ml) were charged into a 2500 ml, 3-necked round-bottom flask equipped with mechanical stirrer, condenser, and therometer. The reaction mixture was warmed with stirring to a gentle reflux and held at reflux for 2 hours. Then the mixture was cooled to room temperature and the ethanol removed on a rotating film evaporator. Cold was used to triturate the residue. The resulting crystals were filtered and then recrystallized from boiling water (6000 ml). Finally the product was vacuum dried to a constant weight at 90°–100° C. at 12 mmHg to obtain 152 grams of the desired product (89% yield) having a melting point of 222°–224° C.

It has been found that the acidity of citrus can be lowered and the Brix/acid ratio increased by applying to the citrus an effective amount of the compound 6-amino-2-ethylthio-4-pyrimidinol. This compound can be applied as equivalent alternatives in the form of a water-soluble salt; i.e., sodium, potassium, ammonium, dimethylamine, etc.

In practicing this invention it is important to realize that the acid content tends to fluctuate from plant to plant. Therefore, application of the compound will not result in the same decrease in acidity in the same amount of time. Generally, the compounds should be applied between full bloom and the development of young fruit. However, in some varieties application can be as late as medium-sized fruit.

The compounds are applied at a rate of from 1 to 50 ounces per acre and 2 to 5 ounces is optimal. Above 5 ounces per acre the increase in effect is nominal, especially in view of the increased cost of the compound applied.

The compounds are employed in the form of aqueous solutions or dispersions. Generally, where the application device is a spray gun, boom or other device where the solution is expelled through a narrow orifice by pressure, the application rate is 50 to 200 gallons of solution per acre. Where the application is by means of an air sprayer (e.g. a "speed sprayer"), i.e. the solution is entrained in a fast moving air stream, more concentrated solutions are employed and about 5 to 50 gallons per acre can be used. Regardless of the amount of solution employed, the pounds of active ingredients per acre should be within the ranges described above.

In the aqueous solutions employed, it is preferred to use a surfactant to prevent the solution from forming globules and "rolling off" upon contact with the leaves of the plant. The surfactant level is generally from 0.1 to 15% by volume of the total formulation and 0.1 to 1.5% preferred. Suitable surfactants which can be employed include: sorbitan monolaurate; sorbitan monopalmitate; sorbitan monostearate; sorbitan monooleate; sorbitan trioleate; polyoxyethylene sorbitan monolaurate; polyoxytheylene sorbitan monopalmitate; polyoxytheylene sorbitan monostearate; polyoxyethylene sorbitan tristearate; polyoxyethylene sorbitan monooleate; polyoxyethylene sorbitan trioleate; polyoxyethylene cetyl ether; polyoxyethylene stearyl ether, and polyoxyethylene oleyl ether.

The above materials are commonly available under trade names such as "Tween", "Span", "Brij", and "Carbowax." Other surfactants which reduce surface tension can also be employed.

In order to demonstrate the usefulness of 6-amino-2-ethylthio-4-pyrimidinol in lowering the acidity and increasing the Brix/acidity ratio in citrus, tests were performed on Hamlin variety oranges. In the tests, the results are shown by the Brix readings, coloring and acid content. The Brix value is determined by randomly selecting one or more citrus fruit, squeezing out the juice, and filtering if necessary to remove solids, and "reading" the juice with a hand refractometer to determine the % Brix. The results of these experiments are as follows:

EXAMPLE 2

| Concentration ppm | Brix | Acids | Brix/Acid Ratio |
| --- | --- | --- | --- |
| 1000 | 9.75 | 0.48 | 20.31 |
| Control | 10.75 | 0.90 | 11.94 |

In the same tests, lead arsenate standards are found to have an average Brix/acid ratio of 22.08, varying from 18.51 to 25.95.

We claim:

1. A method of lowering the acidity and increasing the Brix/acidity ratio of citrus which comprises applying to the citrus an effective amount of 6-amino-2-ethylthio-4-pyrimidinol or its water-soluble salt.

2. The method of claim 1 wherein the amount of 6-amino-2-ethylthio-4-pyrimidinol or its water-soluble salt is from about 1 to about 50 ounces per acre.

3. The method of claim 2 wherein the 6-amino-2-ethylthio-4-pyrimidinol or its water-soluble salt is applied to the citrus plant at from full bloom to medium-sized fruit.

4. The method of claim 1 wherein the citrus is oranges.

5. The method of claim 1 wherein the citrus is grapefruit.

6. The method of claim 1 wherein the citrus is lemons.

7. The method of claim 1 wherein the citrus is tangerines.

8. The method of claim 1 wherein the compound applied to the citrus is 6-amino-2-ethylthio-4-pyrimidonol.

9. The method of claim 1 wherein the compound applied to the citrus is the sodium salt of 6-amino-2-ethylthio-4-pyrimidinol.

10. The method of claim 1 wherein the compound applied to the citrus is the ammonium salt of 6'-amino-2-ethylthio-4-pyrimidinol.

11. The method of claim 1 wherein the compound applied to the citrus is the dimethylamine salt of 6-amino-2-ethylthio-4-pyrimidinol.

* * * * *